United States Patent [19]

Brossi

[11] Patent Number: 4,692,463

[45] Date of Patent: Sep. 8, 1987

[54] ANTIINFLAMMATORY 2,3-DIDEMETHYLCOLCHICINE AND ADDITIONAL DERIVATIVES

[75] Inventor: Arnold Brossi, Bethesda, Md.

[73] Assignee: The United States of America as represented by the Department of Health and Human Services, Washington, D.C.

[21] Appl. No.: 802,680

[22] Filed: Nov. 29, 1985

Related U.S. Application Data

[63] Continuation-in-part of Ser. No. 705,709, Feb. 26, 1985, abandoned.

[51] Int. Cl.[4] .................... A61K 31/36; A61K 31/16
[52] U.S. Cl. .................................. 514/463; 514/510; 514/629; 549/432; 560/139; 564/222; 564/426
[58] Field of Search ................ 564/222, 426; 560/139; 549/432; 514/629, 463, 510

[56] References Cited

U.S. PATENT DOCUMENTS 2,820,029  1/1958  Muller et al. ..................... 564/222
3,997,506  12/1976  Dugat ................................ 564/222

OTHER PUBLICATIONS

Capraro and Brossi, "Tropolonic Colchicum Alkaloids", *The Alkaloids*, vol. 23, Academic Press, 1984, pp. 35-36.

*Primary Examiner*—Dolph H. Torrence
*Attorney, Agent, or Firm*—John S. Roberts, Jr.

[57] ABSTRACT

The present invention describes the finding of potent antiinflammatory properties in 2,3-didemethylcolchicine and its analogs.

8 Claims, No Drawings

ANTIINFLAMMATORY 2,3-DIDEMETHYLCOLCHICINE AND ADDITIONAL DERIVATIVES

This is a continuation-in-part application of pending Ser. No. 705,709 filed Feb. 26, 1985, abandoned.

The present invention describes the finding of potent antiinflammatory properties in 2,3-didemethylcolchicine and its analogs. Especially in the most preferred compound it shows relatively low acute toxicity in experimental animals in comparison to colchicine, and thus is a useful agent in the treatment of rheumatic disorders.

MATERIAL INFORMATION DISCLOSURE

Capraro and Brossi, "Tropolonic Colchicum Alkaloids," *The Alkaloids*, Vol. 23, Academic Press, 1984, pp 35-36. The chemical conversion of colchicine and its congeners into the racemate is well known. Pages 35-36 show the conversion of the (−) optical isomer into the racemate and subsequent conversion to the (+) isomer. The (−) isomer, of course, is the active one which is of interest here.

U.S. Pat. No. 3,997,506 Dugat—Anti-mitotic and anti-gout derivatives of thiocolchicine.

GENERAL PREPARATION

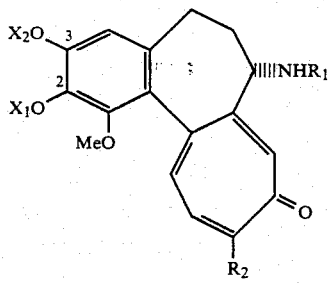

$X_1=X_2=$H or Acyl or $X_1-X_2=-CH_2-$;
$R_1=$Alkyl or Acyl;
$R_2=OCH_3$ or H.

For the compound 2,3-didemethylcolchicine in the above formula $X_1$ and $X_2$ are H; $R_1$ is $COCH_3$; and $R_2$ is $OCH_3$.

The compounds noted in the formula above can be obtained from 3-demethylcolchicine, itself a natural alkaloid, but also obtainable from natural colchicoside by ether cleavage with 85-88% phosphoric acid. Cleavage of the 2-$OCH_3$ group in 3-demethylcolchicine can be achieved with concentrated mineral acids, such as sulfuric acid at temperatures between 50°-9°, or by the action of Lewis acids such as $BBr_3$ or $AlCl_3$ at room temperature or slightly lower temperatures in solvents such as methylenechloride. The 2,3-didemethyl compounds obtained as major products can be separated from other reaction products by chromatographic procedures. Acylation of the 2,3-diphenols can be accomplished with anhydrides in pyridine solution, or in methylenechloride in the presence of potassium carbonate with dimethylaminopyridine as a catalyst. Methylenation of the 2,3-diphenols can be accomplished by treatment with methylenebromide or bromochloromethane in an appropriate solvent such as 1-methylpyrrolidinone. The chemistry mentioned can also be executed with thiocolchiocoside and derived 2,3-didemethylthiocolchicine, which after methylenation and reductive removal of the $SCH_3$ group afford 10-desmethoxy compounds which are also covered by this invention.

Removal of the thiomethyl group can be achieved with Raney-nickel in solvents such as acetone, or zinc in methanol, in the presence of ammonium chloride, and the desthiomethyl-compound can be obtained after usual workup and purified by chromatography.

Exchange of the N-acetyl group in 2,3-didemethylcolchicine can be achieved with simultaneous racemization, by refluxing the compound with acid anhydrides such as butyric anhydride, trifluoroacetic anhydrides, etc. The compounds are isolated by evaporation of solvent by chromatography and isolated as racemic mixtures, containing 50% of the natural (−)—and 50% of the unnatural (+)—antipodes. Removal of the acyl group on the hydroxy groups at 2,3-position can be achieved by mild hydrolysis with potassium carbonate in methanol, or treatment with basic alumina in methylenechloride solution. Separation into optical antipodes can be achieved with a Pirkle column which separates the unnatural from the natural isomer on the optically active column by published procedures (A. Brossi, *J. Nat. Prod.*, 48:878-893, 1985).

All compounds described in this application are potent inhibitors of leukocyte migration which plays an important role in rheumatoid arthritis and other rheumatic disorders. The compounds show in comparison to colchicine little acute toxicity in experimental animals and are for this reason of interest as drugs. Formulation can be achieved by mixing the active ingredients with inert materials to form tablets intended for oral use, or by dissolving the active ingredient in an appropriate solvent for i.p. or i.m. injection. Such solvents are aqueous ethanol, cellosolve or glycerol and other commonly used solvents.

The compounds specifically disclose as active ingredients and utility as tablets and injectable solutions and are used in the form of the (−) isomer. Specific compounds which are a part of this invention are:

(−)-2,3-Didemethylcolchicine
(−)-2,3-Diacetoxydidemethylcolchicine
(−)-Cornigerine [or 2,3-(methylenedioxy)-2,3-didemethoxycolchicine]
(−)-10-Desmethoxycornigerine
(−)-2,3-Dibutyroxy-N-butyryl-deacetylcolchicine
(−)-2,3-Didemethyl-N-butyryl-deacetylcolchicine Colchicine has a variety of biological effects (Capraro and Brossi, *The Alkaloids*, Vol. 23, 1984, Academic Press, pp. 48-57). Besides binding to tubulin protein and causing mytosis by inhibiting tubulin polymerization, colchicine also has antiinflammatory activity, caused by inhibiting migration of white blood cells (granulocytes) to the inflamed area and reducing lactic acid produced when toxic materials bind with white blood cells (phagocytosis). The problem with colchicine, thiocolchicine and many of their analogs is their toxicity which results in a very narrow therapeutic index. Another problem is that colchinoids exert too many biological effects.

The antiinflammatory properties of colchinoids can be evaluated in a classical screening that measures the reduction of swelling produced by injecting (i.p.) carrageenin into the footpad of mice or rats and drug treatment. The drugs can be given orally or intraperitoneally.

It can be seen from the following Table of sample runs that colchinoids with modified 2,3-substitution and specially 2,3-didemethylcolchicine are much less toxic can colchicine itself and also bind less to tubulin protein in vitro. The classical drugs phenybutazone and indomethacine are only active at levels of 100 mg/kg or more.

TABLE

| | Dose mg/kg i.p. | Reduction of Swelling | | Toxicity[1] | T.B. in %[2] |
|---|---|---|---|---|---|
| | | 3 hrs[3] | 5 hrs[3] | | |
| Colchicine | 2 | 44 | 45 | 2.5 | 90 |
| Cornigerine | 2 | 44 | 47 | 39 | 60 |
| 2,3-Didemethyl-colchicine | 2 | 70 | 60 | 54 | 52 |

[1]Measured in the P388 screen and defined as dose which caused average weight loss in mice of 3 g or more.
[2]For details see J. Med. Chem., 26:1367 (1983).
[3]Measured after 3 and 5 hours after i.p. injection of 2% carrageenin solution. Drug given in carrageenine or thyrode solution by i.p. injection.

EXAMPLE 1

3-Demethylcolchicine

Colchicocide (8 g) in polyphosphoric acid (64 ml, 85–88%) was dissolved by gentle heating and stirred at room temperature for 24 hours. The reaction mixture was cooled in an ice bath and the pH adjusted by the addition of 20% NaOH (pH 5). The aqueous layer was extracted with a mixture of $CH_2Cl_2$:isopropanol (3:1, 4×100 ml). The combined organic extracts were washed with water, dried ($Na_2SO_4$) and concentrated to a yellow solid which was washed with 10 ml acetone on a filter to afford 5.7 g material.

EXAMPLE 2

2,3-Didemethylcolchicine (DDC)

A solution of 5.6 g 3-demethylcolchicine in concentrated sulfuric acid (19 ml) was heated for 1.5 hrs at 85°–90° bath temperature. After cooling, the sulfuric acid was adjusted to pH 5 by addition of 10% NaOH, the aqueous solution washed with $CH_2Cl_2$ (1×20 ml), and extracted with a mixture of $CH_2Cl_2$:isopropanol (3:1, 10×50 ml). The combined organic extracts were dried ($Na_2SO_4$) to yield after evaporation in vacuo 3.6 g of a solid. This material was purified on a 6-inch silica gel column. After elution with $CH_2Cl_2$ and $CH_2Cl_2$ containing 10% MeOH, the diol was isolated with $CH_2Cl_2$ containing 15% MeOH. The orange solid obtained after evaporation and trituration with isopropanol gave 2.6 g of crude diol (m/e 372, $^1$H-NMR ($CDCl_3$) C-1 OMe δ 3.43; C-10 OMe δ 3.84).

The crude material was purified by further chromatography on silica gel. The material was added as a slurry together with silica gel and eluted with $CH_2Cl_2$:MeOH=94:6. The material obtained was crystallized from methanol to afford 610 mg of pure yellow DDC of mp 224°; $[α]_D^{20} = -251.4°$ (c 0.5, MeOH). NMR showed signals for the aromatic proton and the two protons of the tropolone ring.

From the mother liquor, another 330 mg of TLC-pure DDC should be obtained. Further elution of the above silica gel column with $CH_2Cl_2$:MeOH=90:10, afforded a material which was more polar: mp 240° (dec), $[α]_D^{20} = -125°$ (c 0.5, MeOH). m/e 403.

EXAMPLE 3

3-Demethylthiocolchicine

A solution of thiocolchicoside (2.3 g, 3.96 mmol) in phosphoric acid (85–88%, 65 ml) after dissolving by heating, was stirred at room temperature for overnight. The TLC analysis showed the absence of thiocolchicoside in the reaction mixture, (one small drop of reaction mixture was diluted with MeOH (0.5 ml) and applied to a TLC plate and run in solvent system A). The reaction mixture was poured on ice, adjusted to pH 5 by the addition of 15% aqueous NaOH solution, followed by several extractions with $CH_2Cl_2$ (4×25 ml). The combined organic layers were dried ($Na_2SO_4$) and evaporated to afford a residue, which was crystallized with acetone to afford 3-demethylthiocolchicine as a yellow solid (1.5 g, 93%), mp 316° C.; $[α]_D^{25} = -251°$ (c 0.21, $CHCl_3$); IR ($CHCl_3$) cm$^{-1}$; 3440 (OH); CIMS: m/e 402 (M++1); Anal. Calcd. for $C_{21}H_{23}NO_5S$: C, 62.82; H, 5.77; N, 3.48; S, 7.98. Found C, 63.09; H, 5.86; N, 3.26; S, 8.25%.

EXAMPLE 4

2,3-Didemethylthiocolchicine

A solution of 3-demethylthiocolchicine (2.0 g) in conc. $H_2SO_4$ (14 ml) was heated in an oil bath to 85°–90° bath temperature for 20 minutes. The dark brown reaction mixture was diluted with $H_2O$ (5 ml) and the pH brought to 5 by the addition of 15% aqueous NaOH. The aqueous layer was extracted with $CH_2Cl$:isopropanol (3:1) 6×10 ml and the combined organic layers dried ($Na_2SO_4$) and concentrated in vacuo to give 1.5 g of a solid which was chromatographed through a silica gel column with the material added in a dry mixture with $SiO_2$. Elution with $CH_2Cl_2$:MeOH (99:1) and (98:2) afforded impure foreruns, and pure material was obtained with $CH_2Cl_2$:MeOH (94:6), which gave almost pure diol after trituation with ethyl acetate (900 mg). M.p. 200°–201°, $[α]_D^{20} = -347.8°$ (c=0.27, MeOH).

EXAMPLE 5

Thiocornigerine

A mixture of the diol from above, anhydrous potassium carbonate (3.3 g), 1-methyl-2-pyrrolidone (17 ml) and bromochloromethane (3.3 ml) was heated at 70° oil bath temperature under argon atmosphere for 20 hours. The reaction mixture was diluted with water (10 ml) and extracted with $CH_2Cl_2$ (4×20 ml). The combined organic phases were washed with water (2×5 ml), dried ($Na_2SO_4$) and concentrated to afford a solid residue still containing pyrrolidone which was removed under high vacuum. The yellow residue was chromatographed on 10 g silica gel, first with $CH_2Cl_2$ to remove an impurity, and then with $CH_2CL_2$:MeOH (99:1), to afford a yellow material. After trituration with ether 410 mg of thiocornigerine was obtained as canary yellow solid: mp 140°, $[α]_D^{20} = -155°$ (c 0.65, $CHCl_3$), $^1$H-NMR: The NMR values of thiocornigerine are as follows: ($CDCl_3$): o 7.25–6.40 (m, 4H, 4x Ar.H), 6.00 (s 2H $OCH_3O$), 4.60 (m, 1H, $C_7$-H), 3.75 (s, 3H, $C_4$-OMe), 2.45 (s, 9H), m/e 400 (M++1).

EXAMPLE 6

10-Desmethoxycornigerine

To a solution of 300 mg thiocornigerine in dry acetone (30 ml) was added freshly prepared Raney-nickel catalyst (8 g) and the reaction mixture treated as described in the preparation of colchicide from thiocolchicine (*J. Med. Chem.*, 26:1369, 1983). After completion of the reaction, the catalyst was filtered, the solution evaporated, and the residue chromatographed as described for colchicide. The first eluate obtained with methylenechloride-methanol mixtures (9:1) afforded 10-desmethoxycornigerine, followed by hexahydrocolchicine as the second material.

EXAMPLE 7

2,3-Diacetyl-2,3-didemethylcolchicine

A small amount of 2,3-diol 2,3-dimethylcolchicine (40 mg) was characterized by acetylation by use of the conditions for the preparation of 1,2-diacetyl-1,2-didemethylcolchicine. The material was crystallized from ethylacetate-ether: mp 207°-208°, $[\alpha]_D^{20} = -113°$ (c 0.2, CHCl$_3$); mass spectrum (CI), m/e 455; NMR (100 MHz, CDCl$_3$) δ 1.96 (s, 3, N-COCH$_3$), 2.31 and 2.33 (2 s, 2×3.2-OCOCH$_3$, and 3-OCOCH$_3$), 3.57 (s, 3, 1-OCH$_3$), 3.99 (s, 3, 10-OCH$_3$).

EXAMPLE 8

2,3-(Methylenedioxy)-2,3-didemethoxycolchicine, Cornigerine

A stirred mixture of 250 mg of 2,3-dimethylcolchicine, 1 g of K$_2$CO$_3$, 1 mL of bromochloromethane, and 5 mL of 1-methyl-2-pyrrolidinone was heated under an N$_2$ atmosphere to 70° C. for 2.5 h. After the mixture was cooled, water was added and the solution extracted with CH$_2$Cl$_2$. The combined extracts were washed (brine), dried (Na$_2$SO$_4$), and evaporated. Residual 1-methyl-2-pyrrolidinone was stripped at high vacuum. The slight brown residue crystallized on addition of ether to give 215 mg of crude 2,3-methylenedioxy compound. The crude material was dissolved in CH$_2$Cl$_2$ and purified by filtration over basic Al$_2$O$_3$ (activity I, 1.5 cm i.d.×12 cm column). After a 50 mL fraction of CH$_2$Cl$_2$ was discarded, the product was eluted with 50 mL of CH$_2$Cl$_2$/MeOH (99:1). Evaporation of solvents and crystallization from CH$_2$Cl$_2$/ether or ethyl acetate/ether gave pure 2,3-(methylenedioxy)-2,3-didemethoxycolchicine: mp 263°-264° C. dec (natural cornigerine, mp 256° C., mmp 263°-264° C. dec); $[\alpha]_D^{22} -149.8°$ (c 0.623, CHCl. Anal. Calcd for C$_{21}$H$_{21}$NO$_6$·0.5H$_2$O: C, 64.28; H, 5.65; N, 3.57. Found: C, 64.26; H, 5.83; N, 3.34.

EXAMPLE 9

Racemization of natural colchicine 10 g colchicine was refluxed in acetic anhydride for 24 hrs. After cooling to room temperature 17 ml water was added and the mixture was refluxed for 12 hrs. After evaporation to dryness, the residue was treated with 40 ml ethylacetate. Insoluble racemic colchicine was obtained after crystallization from acetic acid/water in 62% yield. Mp 280°-282°.

EXAMPLE 10

Racemization of (−)-3-demethylcolchicine (2)

Using the same procedure as for colchicine, after evaporating the solvents 10 ml of a 10% methanolic K$_2$CO$_3$ solution was added and the mixture stirred for 1 h. The MeOH was evaporated and cold 2N HCl was added until pH 6-7. Extraction with CHCl$_3$, washing with brine, drying and evaporating gave a brown residue which was purified by flash chromatography (CHCl$_3$/MeOH 100:7) and crystallized from CHCl$_3$: 2 as a light yellow solid, (51% yield), mp 246°-248° C., $[\alpha]_D^{25}$ 0° (c 0.12, MeOH).

EXAMPLE 11

(±)-2,3-Didemethylcolchicine

The mixture of 126 mg (0.32 mmol) of 2 and 5 ml of conc. H$_2$SO$_4$ was heated at 55°-60° for 7 h. The reaction mixture was cooled and extracted with seven portions of CHCl$_3$/isopropanol 3:1, washed with brine, dried and evaporated. The dark yellow residue was purified by flash chromatography (CHCl$_3$/MeOH 100:8) and crystallized from MeOH/ether. 20 mg (17%) of (±)-2,3-didemethylcolchicine as yellow crystals, mp 277°-279° dec.

EXAMPLE 12

(±)-N-Butyryldeacetylcolchicine

A mixture of 5 g (1.25 mmol) of colchicine and 50 ml of butyric anhydride was refluxed for 5 h. After cooling 10 ml of H$_2$O were added and the solution was refluxed overnight. After evaporation of the solvents, saturated NaHCO$_3$ solution and 20 ml of ethylacetate were added and stirring was continued for 30 min. The two phases were separated and the organic layer washed with brine. After evaporation, the residue was filtered first through a column of neutral alumina (CHCl$_3$/MeOH 100:7) and then purified by flash chromatography (CHCl$_3$/MeOH 100:3). To get rid of the black color the residue was taken up in CHCl$_3$ and treated with charcoal. Filtration over Celite, evaporation and crystallization from aqueous acetone gave 1.17 g (23%) of (±)-N-butyryldeacetylcolchicine as light yellow crystals, mp 145°-147° C., $[\alpha]_D^{25} = 0°$ (c 1.23, CHCl$_3$).

Treatment of (±)-N-butyryldeacetylcolchicine with sulfuric acid, or Lewis acids such as aluminum chloride or boron tribromide in solvents such as dichloromethane or chloroform, affords mixtures of catechols from which the desired (±)-2,3-didemethyl-N-butyryldeacetylcolchicine are isolated by chromatography.

The following formulas show the reaction scheme for Examples 3-5.

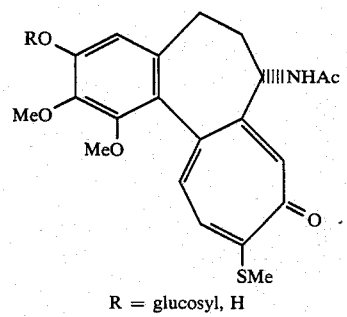

R = glucosyl, H

↓

-continued

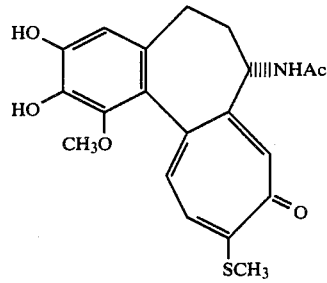

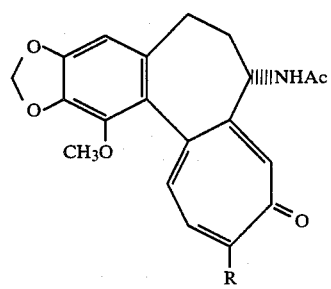

R = SCH₃, H

The following formulas show the reaction scheme for Examples 2 and 7.

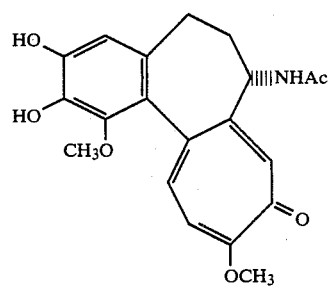

-continued

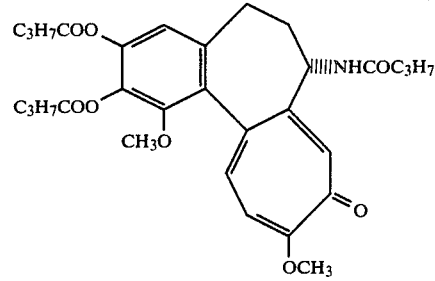

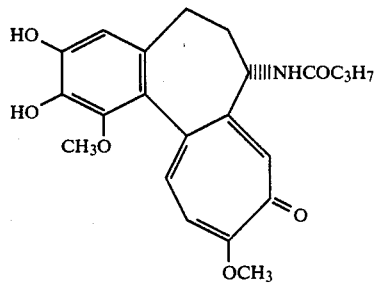

I claim:

1. A method of treating inflammatory disorders in a mammal which comprises injecting said mammal with an effective anti-inflammatory amount of an anti-inflammatory agent set out below

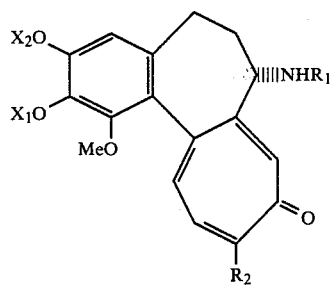

$X_1=X_2=H$ or Acyl or $X_1-X_2=-CH_2-$;
$R_1=$acyl;
$R_2=OCH_3$.

2. A method of treating according to claim 1 wherein the method of treatment consists of injecting intraperitoneally into the footpad of a mouse or rat a pharmaceutical amount of the anti-inflammatory agent in claim 1.

3. The method of claim 1 wherein the anti-inflammatory agent is (−)-2,3-di-demethylcolchicine.

4. The method of claim 1 wherein the anti-inflammatory agent is (−)-2,3-di-acetoxydidemethylcolchicine.

5. The method of claim 1 wherein the anti-inflammatory agent is (−)-cornigerine.

6. The method of claim 1 wherein the anti-inflammatory agent is (−)-2,3-di-butyroxy-N-butyryl-deacetylcolchicine.

7. The method of claim 1 wherein the anti-inflammatory agent is (−)-2,3-demethylN-butyryl-deacetylcolchicine.

8. The method of claim 1 wherein the anti-inflammatory agent is (±)-2,3-di-demethylcolchicine.

* * * * *